United States Patent [19]
Dutkiewicz et al.

[11] Patent Number: 5,599,916
[45] Date of Patent: Feb. 4, 1997

[54] CHITOSAN SALTS HAVING IMPROVED ABSORBENT PROPERTIES AND PROCESS FOR THE PREPARATION THEREOF

[75] Inventors: Jacek Dutkiewicz, Appleton, Wis.; Xin Ning, Alpharetta, Ga.; Jian Qin, Appleton; Tong Sun, Neenah, both of Wis.

[73] Assignee: Kimberly-Clark Corporation, Neenah, Wis.

[21] Appl. No.: 362,395

[22] Filed: Dec. 22, 1994

[51] Int. Cl.$^6$ .................................................. C08B 37/08
[52] U.S. Cl. .......................... 536/20; 536/55.3; 536/124; 424/443; 424/488
[58] Field of Search .......................... 536/20, 124, 55.3; 424/443, 488

[56] References Cited

U.S. PATENT DOCUMENTS

| | | | |
|---|---|---|---|
| 4,029,727 | 6/1977 | Austin et al. | 264/186 |
| 4,195,175 | 3/1980 | Peniston et al. | 536/20 |
| 4,308,377 | 12/1981 | Koshugi | 536/20 |
| 4,431,601 | 2/1984 | Kifune et al. | 264/186 |
| 4,493,928 | 1/1985 | Koshugi | 536/20 |
| 4,570,629 | 2/1986 | Widra | 604/304 |
| 4,572,906 | 2/1986 | Sparkes et al. | 514/21 |
| 4,574,150 | 3/1986 | Austin | 536/20 |
| 4,619,995 | 10/1986 | Hayes | 536/20 |
| 4,833,237 | 5/1989 | Kawamura et al. | 536/20 |
| 4,861,527 | 8/1989 | DeLucca et al. | 264/186 |
| 4,895,724 | 1/1990 | Cardinal et al. | 424/418 |
| 4,929,722 | 5/1990 | Partain, III et al. | 536/20 |
| 4,931,271 | 6/1990 | Lang et al. | 424/47 |
| 4,956,350 | 9/1990 | Mosbey | 514/55 |
| 4,996,307 | 2/1991 | Itoi et al. | 536/20 |
| 5,021,207 | 6/1991 | De Lucca et al. | 264/186 |
| 5,079,354 | 1/1992 | Gross et al. | 536/111 |
| 5,247,072 | 9/1993 | Ning et al. | 536/97 |

FOREIGN PATENT DOCUMENTS

| | | |
|---|---|---|
| 731146 | 4/1963 | Canada . |
| 2072918 | 8/1993 | Canada . |
| 2124665 | 12/1994 | Canada . |
| 0538904A2 | 4/1993 | European Pat. Off. . |
| 0566118A1 | 10/1993 | European Pat. Off. . |
| 0627225A2 | 12/1994 | European Pat. Off. . |
| 54-011955 | 1/1979 | Japan . |
| 60-135432 | 7/1985 | Japan . |
| 61-44084 | 10/1986 | Japan . |
| 6462302 | 3/1987 | Japan . |
| 1-32241 | 6/1989 | Japan . |
| 1-182302 | 7/1989 | Japan . |
| 1-167302 | 7/1989 | Japan . |
| 1-207216 | 8/1989 | Japan . |
| 1-215836 | 8/1989 | Japan . |
| 3-15464 | 1/1991 | Japan . |
| 5-92925 | 4/1993 | Japan . |
| 2195344A | 4/1988 | United Kingdom . |
| WO93/06136 | 4/1993 | WIPO . |

OTHER PUBLICATIONS

Makromol. Chem., vol. 190, No. 5, May 1989, Basel, pp. 951–960, XP002002627 G. A. F. Roberts et al.: "The formation of gels by reaction of chitosan with glutaraldehyde,".

Draget et al. *Biomaterials* 1992, 13(9), 635–638.

Hudson et al. *Polym. Prepr.* 1990, 31(1), 629–630.

*Primary Examiner*—Gary L. Kunz
*Assistant Examiner*—Kathleen K. Fonda
*Attorney, Agent, or Firm*—John R. Schenian

[57] ABSTRACT

Disclosed is a method for producing a water-swellable, water-insoluble chitosan salt having improved absorption properties. The method involves forming a mixture of a chitosan, water, an acid, and, optionally, a crosslinking agent, recovering the formed chitosan salt from the mixture and, optionally, treating said recovered chitosan salt with heat or under humid conditions.

105 Claims, 1 Drawing Sheet

CHITOSAN SALTS HAVING IMPROVED ABSORBENT PROPERTIES AND PROCESS FOR THE PREPARATION THEREOF

BACKGROUND OF THE INVENTION

1. Field of the Invention

The present invention relates to chitosan salts having improved absorbent properties. Specifically, the present invention relates to chitosan salts having an improved ability to absorb liquid while under an external pressure and a process for the preparation thereof.

2. Description of the Related Art

The use of water-swellable, generally water-insoluble absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials has been described for use as absorbent materials in such personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile. While the natural-based absorbent materials are known for use in personal care products, they have not gained wide usage in such products. The natural-based absorbent materials have not gained wide usage in personal care products, at least in part, because their absorbent properties are generally inferior compared to the synthetic absorbent materials, such as the polyacrylates. Specifically, many of the natural-based materials tend to form soft, gelatinous masses when swollen with a liquid. When employed in absorbent products, the presence of such soft gelatinous masses tends to prevent the transport of liquid within the fibrous matrix in which the absorbent materials are incorporated. This phenomenon is known as gel-blocking. Once gel-blocking occurs, subsequent insults of liquid cannot be efficiently absorbed by the product, and the product tends to leak. Further, many of the natural-based materials exhibit poor absorption properties, particularly when subjected to external pressures.

Chitosan, a deacetylated chitin, is a cation-active, polyprimary amine with diverse applications in fields such as dispersing agents, adhesives, pesticides, waste water treatment, food processing, and wound healing.

Unfortunately, the known modified chitosan materials generally do not possess absorptive properties comparable to many of the synthetic, highly-absorptive materials. This has prevented widespread use of such chitosan materials in absorbent personal care products.

In contrast, the synthetic absorbent materials are often capable of absorbing large quantities of liquid while maintaining a generally stiff, non-mucilaginous character. Accordingly, the synthetic absorbent materials can be incorporated in absorbent products while minimizing the likelihood of gel-blocking.

It is therefore desirable to develop and produce a natural-based, highly absorbent chitosan material having absorptive properties similar to the synthetic, highly absorptive materials and, thus, suitable for use in personal care absorbent products.

SUMMARY OF THE INVENTION

In one aspect, the present invention concerns a water-swellable, water-insoluble chitosan salt. The chitosan salt is characterized in that it exhibits an effective initial Absorbency Under Load (AUL) value.

One embodiment of the present invention concerns a water-swellable, water-insoluble chitosan salt that exhibits an initial Absorbency Under Load value of at least about 14 grams per gram.

In another aspect, the present invention further concerns a process for preparing a water-swellable, water-insoluble chitosan salt that exhibits an effective initial Absorbency Under Load value.

One process of the present invention comprises the steps of preparing a mixture comprising a water-insoluble chitosan, water, and an acid. A chitosan salt is formed and is recovered from the mixture under conditions effective so that the chitosan salt becomes water-swellable and water-insoluble and exhibits desired absorbent properties.

One embodiment of such a process comprises forming a mixture comprising a water-insoluble chitosan, water, and an acid selected from the group consisting of monobasic acids having a $pKa_1$ less than about 6 and multibasic acids having a $pKa_1$ less than about 6 and all $pKa_n$ greater than about 5.5, wherein n is an integer greater than 1. The mixture has an equilibrium pH between about 2 and about 6.5. A chitosan salt is formed and recovered from the mixture. The recovered chitosan salt is water swellable and water insoluble and exhibits an initial Absorbency Under Load value of at least about 14 grams per gram.

Another embodiment of such a process comprises forming a mixture comprising a water-insoluble chitosan, water, and an acid selected from the group consisting of monobasic acids having a pKa less than about 6 and multibasic acids having a $pKa_1$ less than about 6 and all $pKa_n$ greater than about 5.5, wherein n is an integer greater than 1. The mixture has an equilibrium pH between about 2 and about 6.5. A chitosan salt is formed and recovered from the mixture. The recovered chitosan salt is then treated at a temperature and for a time effective to render the chitosan salt water swellable and water insoluble, wherein the water-swellable, water-insoluble chitosan salt exhibits an initial Absorbency Under Load value of at least about 14 grams per gram.

Another embodiment of such a process comprises forming a mixture comprising a water-insoluble chitosan, water, and an acid selected from the group consisting of monobasic acids having a pKa less than about 6 and multibasic acids having a $pKa_1$ less than about 6 and all $pKa_n$ greater than about 5.5, wherein n is an integer greater than 1. The mixture has an equilibrium pH between about 2 and about 6.5. A chitosan salt is formed and recovered from the mixture. The recovered chitosan salt is then treated under humid conditions and for a time effective to render the chitosan salt water swellable and water insoluble, wherein the water-swellable, water-insoluble chitosan salt exhibits an initial Absorbency Under Load value of at least about 14 grams per gram.

Another embodiment of such a process comprises forming a mixture comprising a water-insoluble chitosan salt, water, an acid selected from the group consisting of monobasic acids having a $pKa_1$ less than about 6 and multibasic acids having a $pKa_1$ less than about 6 and all $pKa_n$ greater than about 5.5, wherein n is an integer greater than 1, and a crosslinking agent. The mixture has an equilibrium pH between about 2 and about 6.5. A chitosan salt is formed and recovered, along with the crosslinking agent, from the mixture. The recovered chitosan salt is water swellable and water insoluble and exhibits an initial Absorbency Under Load value of at least about 14 grams per gram.

Another process of the present invention comprises preparing a chitosan salt from a chitosan in a mixture comprising a nonsolvent and recovering the chitosan salt from the mixture, wherein the chitosan salt comprises an amount of the original crystalline structure of the chitosan to be effective so that the chitosan salt exhibits an effective initial Absorbency Under Load.

One embodiment of such a process comprises preparing a mixture comprising a chitosan comprising an original crystalline structure, water, an acid selected from the group consisting of monobasic acids having a $pKa_1$ less than about 6 and multibasic acids having a $pKa_1$ less than about 6 and all $pKa_n$ greater than about 5.5, wherein n is an integer greater than 1, and a nonsolvent that is miscible with water and in which both chitosan and the chitosan salt to be formed are insoluble. The water and the nonsolvent are used in amounts in the mixture effective to result in the chitosan and the chitosan salt to be formed not being soluble in the mixture. The mixture has an equilibrium pH between about 2 and about 6.5. A chitosan salt is formed and recovered from the mixture. The recovered chitosan salt is water swellable and water insoluble and exhibits an initial Absorbency Under Load value of at least about 14 grams per gram.

DETAILED DESCRIPTION OF THE PREFERRED EMBODIMENTS

Figure 1:
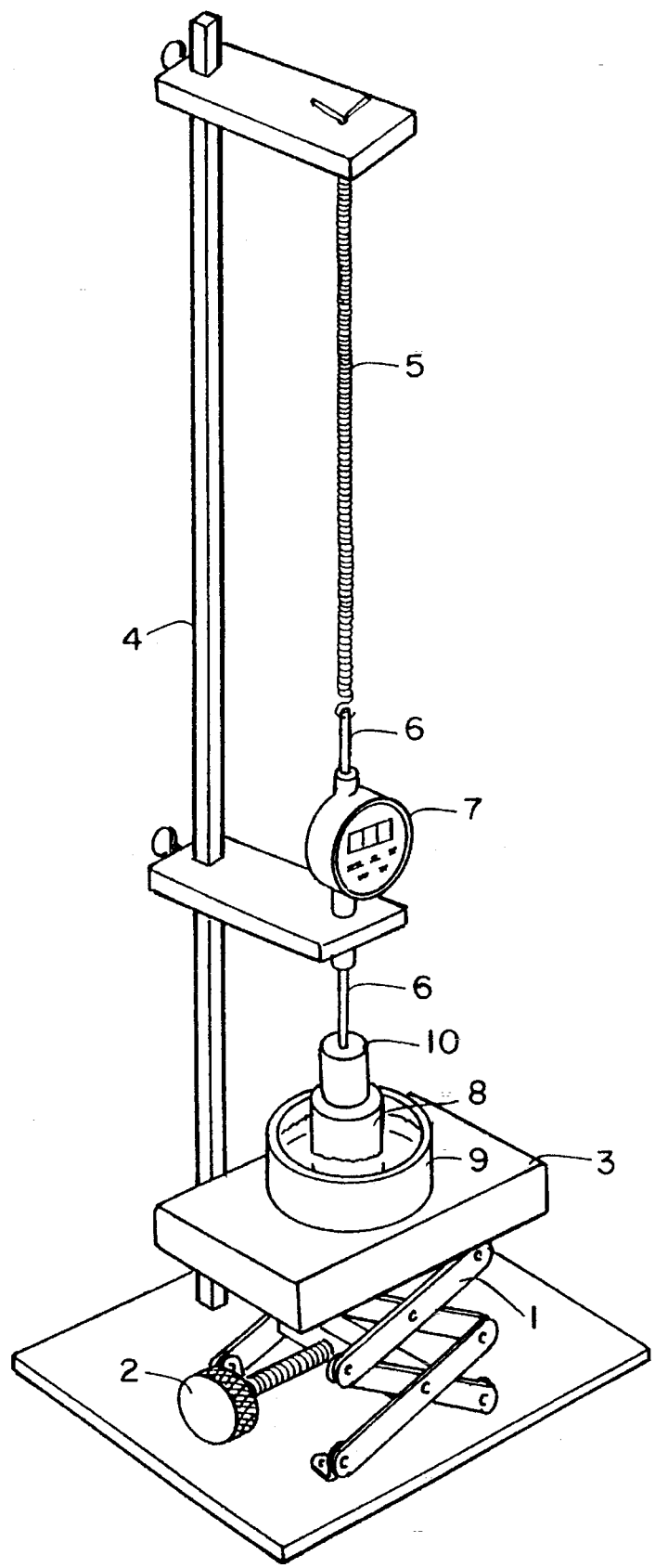
FIG. 1 illustrates the apparatus for determining the Absorbency Under Load values of an absorbent material.

Chitin is a cellulose-like material that occurs widely in nature, for example, in the cell walls of fungi and the hard shell of insect and crustaceans. The waste from shrimp, lobster, and crab seafood industries typically contains about 10 to about 15 percent chitin and is a readily available source of supply. In the natural state, chitin generally occurs only in small flakes or short fibrous material, such as from the carapace or tendons of crustaceans. There is generally no source, as with cotton in the cellulosics, that forms useful shaped articles without solution and re-precipitation or re-naturing.

More specifically, chitin is a mucopolysaccharide, poly-N-acetyl-D-glucosamine with the following formula:

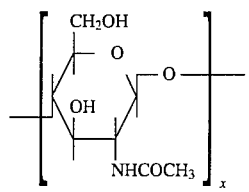

wherein x represents the degree of polymerization. Although x cannot be determined precisely, x is believed to be commonly in the range of from about 50 to about 50,000.

When many of the acetyl groups of chitin are removed by treatment with strong alkalis, the product is chitosan, a high molecular weight linear polymer of 2-deoxy-2-amino glucose. The properties of chitosan relate to its polyelectrolyte and polymeric carbohydrate character. Thus, it is generally insoluble in water, in alkaline solutions at pH levels above about 6.5, or in organic solvents. It generally dissolves readily in dilute solutions of organic acids such as formic, acetic, tartaric, and citric acids, and also in dilute mineral acids, except, for example, sulfuric acid. In general, the amount of acid required to dissolve chitosan is approximately stoichiometric with the amino groups.

Chitosan is thus not a single, definite chemical entity but varies in composition depending on the conditions of manufacture. It may be equally defined as chitin sufficiently deacetylated to form soluble amine salts. Solutions of chitosan are generally highly viscous, resembling those of natural gums. The cationic properties of the polymer lead to the formation of complexes with anionic polyelectrolytes.

The chitosan used herein is suitably in relatively pure form. Methods for the manufacture of pure chitosan are well known. Generally, chitin is milled into a powder and deminerilized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until a generally neutral pH is reached.

Suitable chitosans are commercially available from numerous vendors. Exemplary of a commercially available chitosan is a partially deacetylated chitin, having a degree of acetylation of about 0.2 and a viscosity as a 1 weight percent aqueous solution of about 3,600 centipoise, available from the Vanson Company.

In one aspect, the present invention concerns a water-swellable, water-insoluble chitosan salt that exhibits effective absorbency properties.

Chitosan salts suitable for use in the present invention are generally water soluble, prior to treatment of the chitosan salt, to provide the chitosan salt with the desired absorbency characteristics as disclosed herein. After such treatment to provide the chitosan salt with the desired absorbency characteristics, the chitosan salt will generally be water swellable and water insoluble.

As used herein, a material will be considered to be water soluble when it substantially dissolves in excess water to form a solution, thereby, losing its initially particulate form and becoming essentially molecularly dispersed throughout the water solution. As a general rule, the water-soluble chitosan salts will be free from a substantial degree of crosslinking, as crosslinking tends to render the chitosan salts water insoluble.

As used herein, the term "water-swellable, water-insoluble" is meant to refer to a material that, when exposed to an excess of a 0.9 weight percent solution of sodium chloride in water, swells to its equilibrium volume but does not dissolve into the solution. As such, a water-swellable, water-insoluble material generally retains its original identity or physical structure, but in a highly expanded state, during the absorption of the aqueous solution and, thus, must have sufficient physical integrity to resist flow and fusion with neighboring particles. A water-swellable, water-insoluble chitosan salt useful in the present invention is one which is effectively crosslinked to be substantially water insoluble but still is initially capable of absorbing at least about 14 times its own weight of a 0.9 weight percent solution of sodium chloride in water when under an applied load of about 0.3 pound per square inch.

Chitosan salts suitable for use in the present invention include, without limitation, those salts formed by the reaction of chitosan and an acid, such as an organic acid or an inorganic acid. Examples of chitosan salts formed with an inorganic acid include chitosan hydrochloride, chitosan hydrobromide, chitosan phosphate, and mixtures thereof. Examples of chitosan salts formed with an organic acid include chitosan formate, chitosan acetate, chitosan propionate, chitosan chloroacetate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids. The most suitable chitosan salts include chitosan hydrochloride, chitosan formate, chitosan acetate, chitosan propionate, and mixtures thereof.

Chitosans useful in preparing the chitosan salts of the present invention generally have an average degree of acetylation (D.A.) from 0 to about 0.5, suitably from 0 to about 0.4, and more suitably from 0 to about 0.3. The degree of acetylation refers to the average number of acetyl groups present on the anhydroglucose unit of the chitosan material. Generally, the maximum average number of acetyl groups that may be present on the anhydroglucose unit of the chitin material is 1.0. When the chitosan has an average degree of acetylation within the range of from 0 to about 0.5, the chitosan is generally water insoluble prior to protonation of the chitosan to provide the chitosan salts with the desired initial absorbency properties of the present invention. However, one skilled in the art will appreciate that other characteristics, such as the actual pattern of acetyl groups of the chitosan, may also have an effect on the water-solubility of the chitosan salt.

Chitosan and chitosan salts may generally have a wide range of molecular weights. Chitosan and chitosan salts having a relatively high molecular weight are often beneficial for use in the present invention. Nonetheless, a wide range of molecular weights is suitable for use in the present invention. It is generally most convenient to express the molecular weight of a chitosan or chitosan salt in terms of its viscosity in a 1.0 weight percent aqueous solution at 25° C. Since chitosan is generally insoluble in water at 25° C., it is common to indirectly measure the viscosity of the chitosan by measuring the viscosity of a corresponding chitosan salt, such as by using a 1 weight percent acetic acid aqueous solution. Chitosan or chitosan salts suitable for use in the present invention will suitably have a viscosity in a 1.0 weight percent aqueous solution at 25° C. of from about 100 centipoise (100 mPa.s) to about 80,000 centipoise (80,000 mPa.s), more suitably from about 500 centipoise (500 mPa.s) to about 80,000 centipoise (80,000 mPa.s), and most suitably from about 1,000 centipoise (1,000 mPa.s) to about 80,000 centipoise (80,000 mPa.s).

The crosslinked chitosan salts exhibiting improved absorbent properties of the present invention have been found to exhibit relatively low aqueous solution viscosities as compared to chitosan salts that do not exhibit the improved absorbent properties of the present invention. For example, when measured as a 1.0 weight percent amount in a 0.9 weight percent sodium chloride (saline) aqueous solution that has been allowed to reach equilibrium at about 25° C. as, for example, after about 18 hours of mixing, the chitosan salts of the present invention have been found to exhibit a viscosity of suitably less than about 400 centipoise, more suitably less than about 300 centipoise, and most suitably less than about 200 centipoise. The chitosan salts of the present invention have been found to exhibit viscosities that are suitably about 50 percent, more suitably about 60 percent, and most suitably about 70 percent less than the viscosity exhibited by an otherwise identical chitosan salt that has not been prepared or treated to exhibit the improved absorbent properties of the present invention. For example, if a chitosan salt that has not been prepared or treated to exhibit the improved absorbent properties of the present invention exhibits a viscosity of about 800 centipoise, a chitosan salt that has been prepared or treated to exhibit the improved absorbent properties of the present invention will suitably exhibit a viscosity of less than about 400 centipoise, more suitably less than about 320 centipoise, and most suitably less than about 240 centipoise.

The process according to the present invention is found to produce an improvement in initial AUL values in chitosan salts over a wide range of molecular weights. While high molecular weight chitosan salts are generally preferred, it is important that improvements in low molecular weight chitosan salts can be achieved. This is because aqueous solutions of high molecular weight chitosan salts exhibit a high viscosity compared to an aqueous solution containing the same concentration of low molecular weight chitosan salts. Thus, for reasons of efficiency, it is often desirable to form an aqueous solution comprising the highest concentration of chitosan salt possible while still being able to effectively work with the aqueous solution.

The chitosan salts of the present invention have the ability to absorb a liquid while the chitosan salt is under an external pressure or load, herein referred to as Absorbency Under Load (AUL). Synthetic polymeric materials, such as polyacrylates, having a generally high ability to absorb while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount in grams of an aqueous solution, containing 0.9 weight percent sodium chloride, a gram of a material can absorb in 60 minutes under a load, for example, of about 0.3 pound per square inch (psi). As a general rule, it is desired that the chitosan salt has an initial Absorbency Under Load value, for a load of about 0.3 psi, of at least about 14, beneficially of at least about 17, more beneficially of at least about 20, suitably of at least about 24, more suitably of at least about 27, and up to about 50 grams per gram. As used herein, the term "initial Absorbency Under Load" is meant to refer to that AUL value exhibited by a material as measured within 1 day after preparation of the material while the material is stored at ambient conditions, such as at about 24° C. and between about 30 to about 60 percent relative humidity.

The conditions under which a chitosan salt is stored have been found to potentially have an impact on the absorbent properties of the chitosan salt as it ages. Even relatively mild conditions, such as ambient conditions, such as about 24° C.

and at least about 30 percent relative humidity, suitably between about 30 to about 60 percent relative humidity, will typically result in a change of the absorbent properties of a chitosan salt as it ages. Typically, storage conditions, such as relatively higher temperatures and/or relatively higher relative humidities, as compared to ambient conditions, may result in quicker and/or more severe change of the absorbent properties of the chitosan salt as it ages.

In one embodiment of the present invention, a chitosan salt will tend to retain its initial AUL value after aging. Specifically, it is beneficial that chitosan salts of the present invention retain greater than about 50 percent, suitably greater than about 70 percent, and more suitably more than about 80 percent of their initial AUL value after aging for about 60 days. Typically, the aging conditions are at ambient conditions, such as at about 24° C. and at least about 30 percent relative humidity. For example, if a chitosan salt of the present invention has an initial AUL value of about 20, that chitosan salt beneficially has an AUL value of at least about 10, suitably of at least about 14, and more suitably of at least about 16, after aging for about 60 days at about 24° C. and at least about 30 percent relative humidity. Otherwise similar chitosan salts tend not to retain their initial AUL value after aging under similar conditions.

Beneficially, the chitosan salts of the present invention retain greater than about 50 percent, suitably greater than about 70 percent, and more suitably greater than about 80 percent, of their initial AUL value after aging for about 20 days at about 24° C. and about 100 percent relative humidity.

As described above, the chitosan salt is suitably a chitosan carboxylate, such as chitosan acetate or chitosan formate, or a chitosan hydrohalide, such as chitosan hydrochloride. Such a chitosan carboxylate or chitosan hydrohalide has an initial Absorbency Under Load value of at least about 14, beneficially of at least about 17, more beneficially of at least about 20, suitably of at least about 24, more suitably of at least about 27, and up to about 50, grams per gram. Beneficially, such a chitosan carboxylate or chitosan hydrohalide also retains greater than about 50 percent, suitably greater than about 70 percent, and more suitably greater than about 80 percent, of its initial AUL value after aging for about 60 days at about 24° C. and at least about 30 percent relative humidity and, beneficially, retains greater than about 50 percent, suitably greater than about 70 percent, and more suitably greater than about 80 percent of its initial AUL value after aging for about 20 days at about 24° C. and about 100 percent relative humidity.

Without intending to be bound thereby, it is hypothesized that the aging phenomenon in regards to the AUL is due to the creation of crosslinking points or additional crosslinking points of the chitosan salt. As a result of such crosslinking points or additional crosslinking points, the chitosan salt becomes more rigid or harder, resulting in the chitosan salt becoming less absorbent. Crosslinking points can generally be divided into two groups. First, crosslinking points can be of a relatively permanent crosslinking, such as with ester or amide linkages, resulting, for example, from the use of a multicarboxylic crosslinking agent, or with coordination bonding, resulting, for example, from the use of a polyvalent metal ion crosslinking agent, or with physical crosslinks resulting, for example, from a retained crystalline structure. Second, crosslinking points can be of a relatively temporary crosslinking, such as with hydrogen bonding within the chitosan salt. In order to improve the aging stability of the chitosan salt, it is believed to be desirable to essentially maintain the amount of relatively permanent crosslinking that exists within the chitosan salt so that there is neither a substantial increase nor a substantial decrease in the crosslinking of the chitosan salt as it ages.

It has been found that the chitosan salts of the present invention may be prepared by a variety of processes. In general, an aqueous mixture of a water-insoluble chitosan, water, an acid and, optionally, a crosslinking agent is prepared. Such an aqueous mixture generally comprises from about 0.01 to about 90 weight percent, beneficially from about 0.1 to about 30 weight percent, and suitably from about 2 to about 25 weight percent based on total mixture weight of the chitosan. The mixture generally comprises from about 99.99 to about 10 weight percent, beneficially from about 99.9 to about 70 weight percent, and suitably from about 98 to about 75 weight percent based on total mixture weight of the water.

The chitosan is typically mixed with an aqueous solution beneficially comprising at least about 30 weight percent water, suitably about 50 weight percent water, more suitably about 75 weight percent water, and most suitably 100 weight percent water. When another liquid is employed with the water, such other suitable liquids include methanol, ethanol, isopropanol, and acetone. However, the use or presence of such other non-aqueous liquids may impede the formation of a homogeneous mixture such that the chitosan chains do not effectively dissolve into the aqueous solution and interpenetrate one another.

One process of the present invention comprises preparing the chitosan salt from a chitosan comprising an original crystalline structure and retaining an effective amount of the original crystallinity wherein such retained crystallinity functions as a crosslinking moiety so that the chitosan salt exhibits an effective initial Absorbency Under Load value.

In such a process, the chitosan is dispersed in a nonsolvent and an acid and water are added to the mixture. As used herein, the term "nonsolvent" is meant to represent a non-aqueous liquid that is miscible with water and in which both chitosan and the chitosan salt to be formed are insoluble. Examples of nonsolvents useful in the present invention include methanol, ethanol, acetone, isopropanol, dioxane, glycerol, ethylene glycol, propylene glycol, butanol, pentanol, hexanol, and mixtures thereof. Suitable nonsolvents include methanol, ethanol, isopropanol, and mixtures thereof. The water and the nonsolvent are used in amounts in the mixture effective to result in the chitosan and the chitosan salt to be formed not being soluble in the mixture.

The acids are added to the mixture at conditions effective to allow the acids to react with and modify the chitosan to a chitosan salt while retaining an effective amount of the original crystallinity of the chitosan. Such effective conditions can vary and will typically depend on, for example, temperature, pressure, mixing conditions, and types and relative amounts of materials, nonsolvents, water and acids used. The chitosan salt is then generally recovered from the mixture as, for example, using the methods described herein. Such a final recovered crystalline-crosslinked chitosan salt comprises an amount of the original crystalline structure of the chitosan to be effective to result in the crystalline-crosslinked chitosan salt exhibiting an effective initial Absorbency Under Load value.

Chitosan is generally known to be highly crystalline material. The degree of crystallinity generally depends on the source of the chitosan and its processing history. The highly-ordered crystalline structures and the less-ordered amorphous areas generally have different accessibilities toward incoming chemicals such as acids. The result of this difference in accessibility is that the amorphous areas are, in the case of reaction with an acid, generally protonated first and heaviest, whereas the highly crystalline areas are protonated last and least. Swelling of the chitosan improves the accessibility of the acid into the crystalline areas and facilitates the protonation. If the overall degree of protonation of the chitosan is sufficiently high and the protonated amino groups are relatively uniformly distributed, total solubility of the chitosan salt in an aqueous solution is generally achieved. However, if the overall degree of protonation is relatively low, or the protonated amino groups relatively unevenly distributed, the resulting chitosan salt will have a chain structure of alternating soluble and insoluble segments like a block copolymer. The insoluble segments would generally be in the crystalline areas remaining after the protonation. Such a crystalline area functions as a crosslinking point for the soluble chitosan salt segments. Such crystallinity of the initial chitosan or of the chitosan final product may be determined by analytical methods such as optical microscopy and x-ray diffraction.

Such crystalline-crosslinked chitosan salts generally need to be recovered from the nonsolvent mixture but generally do not need any additional processing steps, such as heat or chemical treatment, in order to exhibit the desired initial AUL value absorbency properties described in this invention.

Chitosan salts exhibiting the desired initial Absorbency Under Load properties herein have been found to generally require being prepared by using an acid selected from the group consisting of monobasic acids having a $pKa_1$ less than about 6, multibasic acids having a $pKa_1$ less than about 6 and all $pKa_n$ greater than about 5.5, wherein n is an integer greater than 1, and mixtures thereof. The use of acids not meeting these requirements has been found to result in chitosan salts that generally do not exhibit the desired initial Absorbency Under Load properties. The pKa of an acid represents the extent of dissociation of or, in other words, the strength of the acid and is intended herein to be measured at the conditions, such as at a specific temperature, under which the acid is being used in the process of the present invention. Suitably, the pKa of the acid is measured at about 25° C. In general, the weaker an acid, the higher its pKa value will be. The pKa values for acids at various temperatures are well known and may be found in any of many available references, such as in the CRC Handbook of Chemistry & Physics, 75th Edition, edited by David R. Lide, pages 8–45, CRC Press (1994).

As used herein, the term "monobasic acid" is intended to represent an acid having one displacable hydrogen atom per molecule. The monobasic acids should have a $pKa_1$ less than about 6, suitably less than about 5.5, and more suitably less than about 5 as measured at the conditions under which the acid is being used in the process. Examples of monobasic acids having a $pKa_1$ less than about 6, when the $pKa_1$ is measured at about 25° C., include hydrochloric, hydrobromic, hydrofluoric, hypochlorous, iodic, nitrous, perchloric, periodic, acetic, acetoacetic, acrylic, adipamic, m-aminobenzoic, p-aminobenzoic, o-aminobenzosulfonic, m-aminobenzosulfonic, p-aminobenzosulfonic, anisic, o-β-anisylpropionic, m-β-anisylpropionic, p-β-anisylpropionic, barbituric, benzoic, benzosulfonic, bromoacetic, o-bromobenzoic, m-bromobenzoic, n-butyric, iso-butyric, n-caproic, iso-caproic, chloroacetic, o-chlorobenzoic, m-chlorobenzoic, p-chlorobenzoic, α-chlorobutyric, β-chlorobutyric, γ-chlorobutyric, o-chlorocinnamic, m-chlorocinnamic, p-chlorocinnamic, o-chlorophenoxyacetic, m-chlorophenoxyacetic, o-chlorophenylacetic, m-chlorophenylacetic, p-chlorophenylacetic, β-(o-chlorophenyl)propionic, β-(m-chlorophenyl)propionic, β-(p-chlorophenyl)propionic, α-chloropropionic, β-chloropropionic, cis-cinnamic, trans-cinnamic, crotonic (trans-), cyanoacetic, γ-cyanobutyric, o-cyanophenoxyacetic, m-cyanophenoxyacetic, p-cyanophenoxyacetic, cyanopropionic, dichloroacetic, dichloroacetylacetic, dihydroxybenzoic (2,2-), dihydroxybenzoic (2,5-), dihydroxybenzoic (3,4-), dihydroxybenzoic (3,5-), dihydroxymalic, dihydroxytartaric, dimethylmalonic, dinicotinic, dinitrophenol (2,4-), dinitrophenol (3,6-), diphenylacetic, ethylbenzoic, ethylphenylacetic, fluorobenzoic, formic, fumaric (trans-), furancarboxylic, furoic, gallic, glutaramic, glycolic, heptanoic, hexahydrobenzoic, hexanoic, hippuric, hydroxy acetic, naphthalenesulfonic, α-naphthoic, β-naphthoic, nitrobenzene, o-nitrobenzoic, m-nitrobenzoic, p-nitrobenzoic, o-nitrophenylacetic, m-nitrophenylacetic, p-nitrophenylacetic, o-β-nitrophenylpropionic, p-β-nitrophenylopropionic, nonanic, octanoic, phenylacetic, o-phenylbenzoic, γ-phenylbutyric, α-phenylbutyric, β-phenylpropionic, β-hydroxybutyric, γ-hydroxybutyric, β-hydroxypropionic, iodoacetic, o-iodobenzoic, m-iodobenzoic, lactic, lutidinic, DL-Mandelic, mesitylenic, methyl-o-aminobenzoic, methyl-m-aminobenzoic, methyl-p-aminobenzoic, o-methylcinnamic, m-methylcinnamic, p-methylcinnamic, β-methylglutaric, methylmalonic, picric, pimelic, propionic, iso-propylbenzoic, 2-pyridinecarboxylic, 3-pyridinecarboxylic, 4-pyridinecarboxylic, quinolinic, suberic, sulfanilic, terephthalic, thioacetic, thiophenecarboxylic, o-toluic, m-toluic, p-toluic, trichloroacetic, trihydoxybenzoic (2,4,6-), trimethylacetic, trinitrophenol (2,4,6-), uric, n-valeric, iso-valeric, vinylacetic acids, and mixtures thereof. Suitable monobasic acids having a $pKa_1$ less than about 6, when the $pKa_1$ is measured at about 25° C., include acetic acid, acrylic acid, n-butyric acid, iso-butyric acid, chloroacetic acid, formic acid, hydrobromic acid, hydrochloric acid, hydroxy acetic acid, propionic acid, and mixtures thereof.

In contrast, examples of monobasic acids having a $pKa_1$ greater than about 6, when the $pKa_1$ is measured at about 25° C., include arsenious, hydrocyanic, hydrogen peroxide, hypobromous, hypoiodous, d-alanine, allantoin, alloxanic, α-aminoacetic (glycine), o-aminobenzoic, cacodylic, o-cresol, m-cresol, p-cresol, glycerol, glycine, glycol, histidine, hydroquinone, o-monochlorophenol, m-monochlorophenol, p-monochlorophenol, α-naphthol, β-naphthol, o-nitrophenol, m-nitrophenol, p-nitrophenol, phenol, γ-hydroxyquinoline, lysine, pyrocatechol, resorcinol, saccharin, theobromine, tryptophan, tyrosine, veronal, and xanthine acids.

It is believed that the use of monobasic acids having a $pKa_1$ greater than about 6 generally will not result in chitosan salts exhibiting the desired initial Absorbency Under Load properties because such acids are too weak to sufficiently protonate the chitosan to form the desired chitosan salt.

As used herein, the term "multibasic acid" is intended to represent an acid having more than one displacable hydrogen atom per molecule. Examples of multibasic acids having a $pKa_1$ less than about 6 and all $pKa_n$ greater than about 5.5, wherein n is an integer greater than 1, include arsenic, chromic, o-phosphoric, phosphorous, sulfurous, tellurous, tetraboric, ascorbic, DL-aspartic, cyclohexane-1:1-dicarboxylic, cyclopropane-1:1-dicarboxylic, dimethylmalic, o-hydroxybenzoic, m-hydroxybenzoic, p-hydroxybenzoic, and maleic, and mixtures thereof.

In contrast, examples of multibasic acids that do not have a $pKa_1$ less than about 6 and all $pKa_n$ greater than about 5.5, wherein n is an integer greater than 1, include o-boric, carbonic, germanic, hydrogen sulfide, pyrophosphoric, m-silicic, o-silicic, telluric, adipic, citric, DL-cysteine, L-cystine, fumaric (trans-), glutaric, oxalic, o-phthalic, m-phthalic,, p-phthalic, itaconic, malic, malonic, mesaconic, methylsuccinic, succinic, α-tartaric, and meso-tartaric. Such acids may have a $pKa_1$ greater than about 6 or a $pKa_n$ less than about 5.5.

It is believed that the use of a multibasic acid having a $pKa_1$ greater than about 6 generally will not result in chitosan salts exhibiting the desired initial Absorbency Under Load properties because such acids are too weak to sufficiently protonate the chitosan to form the desired chitosan salt. It is believed that the use of a multibasic acid having a $pKa_n$ less than about 5.5 results in chitosan salts that generally do not exhibit the desired initial Absorbency Under Load properties, because such a multibasic acid essentially acts as a crosslinking agent and generally results in too much crosslinking of the chitosan salt, negatively affecting the desired absorbent properties of the chitosan salt.

Chitosan salts exhibiting the desired retention of Absorbency Under Load properties with aging have been beneficially prepared by using a combination of acids. For example, as compared to using a single acid such as formic acid or acetic acid, improved aged Absorbency Under Load properties have been found to be achieved by using a combination of, respectively, formic acid and hydrochloric acid or acetic acid and hydrochloric acid.

As the chitosan reacts with the acid and is protonated, the chitosan is converted to the corresponding chitosan salt. In contrast to the initial chitosan, which is generally water-insoluble, the formed chitosan salt is generally water soluble. As such, as the chitosan salt is formed in the aqueous solution, the chitosan salt dissolves into the aqueous solution. The dissolution of the chitosan salt into an aqueous mixture is believed to result in entanglement of individual segments of the chitosan salt with each other. Such entanglement results in the chitosan salt chains interpenetrating one another in the mixture so that a random, coil-entangled molecular configuration occurs which is believed to effectively provide crosslinking points and which assists allowing for additional crosslinking, if desired, of the chitosan salt upon further treatment as, for example, with heat treatment or with humidity treatment. To allow for effective entanglement of individual segments of the chitosan salt with each other, the mixture is suitably allowed to form a stable, homogeneous mixture at equilibrium prior to additional treatment steps to ensure effective dissolution of the chitosan salt into the water. It will be appreciated that a nonwater-soluble portion of the chitosan salt may exist that will typically not dissolve into water. For example, the retained crystalline areas of a crystalline-crosslinked chitosan salt will typically not dissolve in water while the non-crystalline areas typically will.

The presence of a crosslinking agent, in certain embodiments of processes of the present invention, may improve the initial Absorbency Under Load value of a chitosan salt when compared to an otherwise essentially identical chitosan salt without a crosslinking agent in an otherwise essentially similar process. As such, a crosslinking agent may optionally be used in the process of the present invention.

Crosslinking agents suitable for use in the present invention are generally water soluble. One suitable crosslinking agent is a compound having at least two functional groups or functionalities capable of reacting with the amido, amino, or hydroxyl groups of a chitosan salt. It is desired that such a crosslinking agent be selected from the group consisting of organic compounds such as dialdehydes, multicarboxylic acids, diepoxides, and mixtures thereof. Specifically, the crosslinking agent may be selected from the group consisting of glutaraldehyde, citric acid, butane tetracarboxylic acid, carboxymethyl cellulose, poly(ethylene glycol) diglycidal ether, and bis[polyoxyethylene bis(glycidyl ether)], and mixtures thereof.

Another suitable crosslinking agent is a multibasic acid having both a $pKa_1$ and a $pKa_2$ that are both less than about 5.5. Such an acid may have more than two displacable hydrogen atoms per molecule wherein the $pKa_m$ is less than or greater than 5.5, wherein m is an integer greater than 2. Examples of such acids useful as crosslinking agents herein include pyrophosphoric acid, adipic acid, butane tetracarboxylic acid, citric acid, glutaric acid, itaconic acid, malic acid, malonic acid, mesaconic acid, methylsuccinic acid, oxalic acid, o-phthalic acid, m-phthalic acid, p-phthalic acid, succinic acid, alpha-tartaric acid, and meso-tartaric acid. Suitably, the crosslinking agent is selected from adipic acid, butane tetracarboxylic acid, citric acid, glutaric acid, itaconic acid, malic acid, succinic acid, and mixtures thereof.

Another suitable crosslinking agent comprises a metal ion with at least two positive charges and which is effective to form coordination bonds with the chitosan salt, such as $Cu^{2+}$, $Fe^{3+}$, $Ce^{3+}$, $Ti^{4+}$, $Zr^{4+}$, and $Ce^{4+}$. Suitable metal ion crosslinking agents include those of the transition elements which generally have vacant d-orbitals. Suitable metal ion crosslinking agents include $CuSO_4$, $ZrCl_4$, $FeCl_3$, $Ce_2(SO_4)_3$, and $Ce(NH_4)_4(SO_4)_4 \cdot 2H_2O$, other well known metal ion compounds and mixtures thereof. Such metal ion crosslinking agents, when used with a chitosan salt, are believed to form chelates with the chitosan salts.

The crosslinking agent is suitably used in an amount of from about 0.01 to about 20, more suitably of from about 0.05 to about 10, and most suitably of from about 0.1 to about 5 weight percent, based on total weight of the chitosan used to prepare the chitosan salt.

In general, a crosslinking catalyst will not be needed, but may be beneficial, to assist in the crosslinking of the chitosan salts of the present invention. Such crosslinking catalysts can be used in an amount of from about 0.01 to about 3.0 weight percent, suitably from about 0.1 to about 1.0 weight percent based on the total weight of the chitosan used. A suitable crosslinking catalyst, for example, is sodium hypophosphite when citric acid is used as the crosslinking agent.

Generally, the order of mixing the chitosan, water, and acid is not critical in the process of the present invention. As such, either the chitosan or the acid may be added to the water and then the remaining materials subsequently added, or all materials may be added together at essentially the same time. However, it may be beneficial to first add the chitosan and water together so that the chitosan may swell so as to make more of the chitosan accessible to the acid. The acid may then be added to the mixture.

When a crosslinking agent is used, it is generally beneficial to add the crosslinking agent after the other materials have been mixed together. This is so that the chitosan does not become crosslinked before it is able to be converted to the desired chitosan salt or that the chitosan salt becomes too crosslinked before it is sufficiently protonated. It is particularly beneficial to add the crosslinking agent after the other materials have been mixed together when the crosslinking agent, such as glutaraldehyde, substantially crosslinks the chitosan salt in the mixture as compared to substantially crosslinking the chitosan salt during a later, post-recovery treatment process.

The aqueous mixture of a chitosan, water, acid, and optionally a crosslinking agent should be prepared under conditions effective to form a chitosan salt. Thus, the mixture can generally be formed at any temperature at which the prepared chitosan salt will be soluble in the water. Generally, such temperatures will be within the range of from about 10° C. to about 100° C. As a general rule, it is suitable to form the mixture with agitation.

It has been found that the aqueous mixture must be acidic in order to achieve a chitosan salt that exhibits the desired absorbent properties of the present invention. In particular, it is desired that the mixture used to prepare the chitosan salts of the present invention have an equilibrium pH between about 2 to about 6.5, suitably between about 2.5 to about 6, and more suitably between about 4 to about 6. Mixtures having an equilibrium pH that is either too low or too high have generally been found to not result in chitosan salts exhibiting the desired absorbent properties. As used herein, the term "equilibrium pH" is meant to represent the pH of the mixture used to prepare the chitosan salt of the present invention when the mixture has reached equilibrium or, in other words, a steady state. In such a mixture at equilibrium, the chitosan will generally have substantially reacted with the acid to form the desired chitosan salt.

The chitosan salts of the present invention are suitable for use in disposable absorbent products such as personal care products, such as diapers, training pants, baby wipes, feminine care products, adult incontinent products, and medical products, such as wound dressings or surgical capes or drapes. When the chitosan salt of the present invention is intended for use in disposable absorbent products, it is typically desired that the chitosan salt have a generally neutral or slightly acid character.

After forming a mixture of chitosan, water, acid, and, optionally, a crosslinking agent, a chitosan salt is formed and is desirably recovered from the mixture. If a crosslinking agent is used, the crosslinking agent should also be recovered with the chitosan salt from the mixture. Any method of recovering the chitosan salt and the crosslinking agent, if used, from the mixture, without unacceptably deteriorating the absorption properties of the chitosan salt, is suitable for use in the present invention. Examples of such methods include evaporative drying, freeze drying, precipitation, critical point drying, and the like.

As used herein, recovery of the chitosan salt and a crosslinking agent, if used, from the mixture is meant to represent that substantially all of the water and, if present, nonsolvent is separated from the chitosan prior to additional treatment steps. It will be appreciated however that, even after removal of substantially all of the water and nonsolvent, a small amount of water and nonsolvent may remain entrapped within the structure of the chitosan salt. The amount of water and nonsolvent remaining entrapped within the structure of the chitosan salt will typically depend on the method and conditions under which the chitosan salt is recovered. Generally, less than about 15 weight percent, suitably less than about 10 weight percent, and more suitably less than about 5 weight percent, of the original amount of water and nonsolvent in the mixture will remain entrapped within the recovered chitosan salt.

Suitably, the chitosan salt and a crosslinking agent, if used, are recovered from the mixture with evaporative drying. As a general rule, the chitosan salt can be recovered by evaporative drying at a temperature within the range of from about 10° C. to about 100° C., suitably from about 40° C. to about 60° C. Naturally, higher temperatures can be employed if the mixture is placed under pressure. Lower temperatures can be employed if the mixture is placed under a vacuum.

Other methods of recovery include precipitation in which a precipitating agent, such as methanol, ethanol, isopropanol, or acetone is added to the mixture to precipitate the chitosan salt and the crosslinking agent, if used, out of the mixture. The chitosan and the crosslinking agent, if used, can then be recovered by filtration. If precipitation is used to recover the chitosan salt, it may be desirable to wash the recovered chitosan salt to remove the precipitating agent.

Depending on the form in which the chitosan salt is recovered, it may be necessary or desirable to alter the form of the chitosan salt. For example, if evaporative drying is employed, the chitosan salt may be recovered in the form of a film or sheet. It may be desirable to comminute the film or sheet material into particles or flakes of material.

The form of the recovered chitosan salt desired will depend to a large extent on the use for which it is intended. When the chitosan salt is intended for use in absorbent personal care products, it is generally desired that the chitosan salt be in the form of a discrete particle, fiber or flake. When in the form of a particle, it is generally desired that the particle have a maximum cross-sectional dimension within the range from about 50 micrometers to about 2,000 micrometers, suitably within the range from about 100 micrometers to about 1,000 micrometers, beneficially within the range from about 300 micrometers to about 600 micrometers.

It may be desirable to treat a chitosan salt, after it has been recovered from the mixture in which it was prepared, under conditions effective to result in the chitosan salt becoming water swellable and water insoluble and exhibiting the desired initial Absorbency Under Load value. In order to prepare such a desired chitosan salt, it may be desirable to use more than one post-recovery treatment methods.

In one embodiment of the process of the present invention, the recovered chitosan salt and the crosslinking agent, if used, are desirably heat treated at an elevated temperature for a period of time. Such heattreatment should be effective to result in crosslinking or additionally crosslinking the chitosan salt effective to achieve the desired initial AUL value as described herein.

In general, if heat treatment is necessary, any combination of temperature and time which is effective in achieving a desired degree of crosslinking, without undesirable damage to the chitosan salt, so that the chitosan salt becomes water swellable and water insoluble and exhibits a desired initial AUL value as described herein, is suitable for use in the present invention. As a general rule, the chitosan salt will be heat treated at a temperature within the range beneficially from about 50° C. to about 250° C., suitably from about 80° C. to about 250° C., more suitably from about 80° C. to about 200° C., and most suitably from about 90° C. to about 140° C. The higher the temperature employed, the shorter the period of time generally necessary to achieve the desired degree of crosslinking.

Generally, the heat treating process will extend over a time period within the range of from about 1 minute to about 600 minutes, beneficially from about 2 minutes to about 200 minutes, and suitably from about 5 minutes to about 100 minutes.

By using an acid that is volatile to prepare the chitosan salt of the present invention, the time necessary to effect the insolubilization of the chitosan salt may be shortened. Without intending to be bound hereby, this is believed to be because evaporation of the volatile acid from the chitosan salt will generally result in there being more free amino groups present so that a relatively more crystallite or highly ordered structure will result that acts as crosslinkage bonds within the structure of the chitosan salt. Providing the mixture with a relatively less volatile acid tends to lengthen the time of the crosslinking process, at a given temperature, compared to the use of a relatively more volatile acid. Nonetheless, similar general absorptive properties can generally be achieved with the use of either a volatile or a nonvolatile acid.

As used herein, a "volatile acid" or "an acid that is volatile" is intended to represent an acid that may be disassociated from the chitosan salt in which the acid is incorporated at a temperature less than about 200° C. In general, a volatile acid will be an acid that has a boiling point less than about 200° C. However, if the acid forms bonds that are too strong within the chitosan salt, such an acid may not be capable of being readily disassociated from the chitosan salt even though the acid has a boiling point less than about 200° C. Thus, for example, hydrochloric acid has a boiling point less than about 200° C. but forms such strong bonds within the chitosan salt that the hydrochloric acid is essentially incapable of being disassociated from the chitosan salt even at temperatures up to about 200° C. Examples of acids suitable for use as a volatile acid herein include formic acid, acetic acid, propionic acid, butyric acid, and mixtures thereof. As used herein, a "nonvolatile acid" is intended to represent an acid that will not be disassociated from the chitosan salt in which the acid is incorporated at a temperature less than about 200° C. In general, a nonvolatile acid will have a boiling point greater than about 200° C. or, as discussed above, has a boiling point less than about 200° C. but forms such strong bonds within the chitosan salt that the acid will not easily disassociate from the chitosan salt. Examples of acids suitable for use as a nonvolatile acid herein include hydrochloric acid or phosphoric acid. In some instances, it may be desired to use both a volatile and a nonvolatile acid in the mixture used to prepare the chitosan salt. For example, a volatile acid, such as formic acid or acetic acid, may be used in combination with a nonvolatile acid such as hydrochloric acid or phosphoric acid.

In one embodiment of the process of the present invention, the recovered chitosan salt and the crosslinking agent, if used, are desirably treated under conditions of humidity for a period of time. Such humidity treatment should be effective to result in crosslinking or additionally crosslinking the chitosan salt effective to achieve the desired initial AUL value as described herein.

In general, if humidity treatment is necessary, any combination of humidity and time which is effective in achieving a desired degree of crosslinking, without undesirable damage to the chitosan salt, so that the chitosan salt becomes water swellable and water insoluble and exhibits a desired initial AUL value as described herein, is suitable for use in the present invention. As a general rule, the chitosan salt will be treated at a humidity within the range beneficially from about 75 percent relative humidity to 100 percent relative humidity, suitably from about 90 percent relative humidity to 100 percent relative humidity, more suitably from about 95 percent relative humidity to 100 percent relative humidity, and most suitably at about 100 percent relative humidity. The higher the humidity employed, the shorter the period of time generally necessary to achieve the desired degree of crosslinking.

Generally, the humidity treating process will extend over a time period within the range of from about 1 day to about 60 days, suitably from about 1 day to about 40 days, and more suitably from about 1 day to about 30 days.

The heat treating or humidity treating processes generally cause the chitosan salt to crosslink or additionally crosslink and become generally water swellable and water insoluble. Without intending to be bound hereby, it is believed that the heat treating or humidity treating process causes the chitosan salt to undergo both physical and chemical crosslinking. Esterification is believed to occur between certain crosslinking agents and the hydroxyl groups of the chitosan salt. In the absence of a crosslinking agent, heat treatment or humidity treatment of the chitosan salt is believed to result in a crystallization of the chitosan salt structure.

There is generally an optimum degree or amount of crosslinking of a particular chitosan salt that optimizes the initial Absorbency Under Load value and, desirably, the aging stability of the particular chitosan salt. If too little crosslinking occurs, the chitosan salt may possess a relatively low initial Absorbency Under Load value due to a lack of gel strength. If too much crosslinking occurs, the chitosan salt may similarly have a relatively low initial Absorbency Under Load value due to the inability of the chitosan salt to absorb liquid.

Any method of recovering the chitosan salt from a mixture, without unacceptably deteriorating the absorption characteristics of the chitosan salt, is suitable for use in the present invention. Examples of such methods include evaporative drying, freeze drying, precipitation, critical point drying, and the like.

Those skilled in the art will recognize that the presence of crosslinks formed by either chemical bonds such, as esterification, or by physical structure crystallization can generally be detected through various analytical techniques. For example, infrared spectroscopy, X-ray diffraction, and nuclear magnetic resonance can be used to verify the presence of chemical bonding and physical structure crystallite crosslinks.

In another aspect, the present invention relates to a water-swellable, water-insoluble chitosan salt characterized in that the chitosan salt possesses crosslinks formed by chemical bonding or physical structure crosslinking. Such a chitosan salt is suitably formed by the methods described above. Nonetheless, the described methods are not intended to be the exclusive methods by which such a chitosan salt can be formed.

Test Methods

Absorbency Under Load

The Absorbency Under Load (AUL) is a test which measures the ability of an absorbent material to absorb a liquid (such as a 0.9 weight percent solution of sodium chloride in distilled water) while under an applied load or restraining force.

Referring to FIG. 1, the apparatus and method for determining AUL will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9 which contains the saline solution to be absorbed. A weight 10 rests on top of a spacer disc (not visible) resting on top of the superabsorbent material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543–180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill., Item No. 9640K41), which serves to counter or reduce the downward force of the probe to about 1 gram±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of about 0.3 pound per square inch. The sample cup is placed in the Petri dish on the platform and the laboratory jack raised up until it contacts the tip of the probe. The meter is zeroed. A sufficient amount of saline solution is added to the Petri dish (50–100 milliliters) to begin the test. The AUL can be determined by determining the weight difference between the sample cup before and after the test, the weight difference being the amount of solution absorbed by the sample. The weight of saline solution absorbed after about 60 minutes is the AUL value expressed as grams saline solution absorbed per gram of absorbent. If desired, the readings of the modified thickness meter can be continuously inputted to a computer (Mitutoyo Digimatic Miniprocessor DP-2 DX) to make the calculations and provide AUL readings. As a cross-check, the AUL can also be determined by determining the distance the 100 gram weight is raised by the expanding sample as it absorbs the saline solution, as measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated.

EXAMPLES

In the examples, various chitosan materials were used as the starting material in the preparation of chitosan salts. For ease of identification, these chitosans are identified by letter, such as by Chitosan A, Chitosan B, and the like. The respective properties of these chitosans are shown in Table 1, in which: D.A. represents the degree of acetylation substitution of the chitosan; Viscosity represents the Brookfield viscosity, in centipoise (cps), of the chitosan as measured at about 23° C. of a 1 weight percent solution in 1 weight percent aqueous acetic acid; Mw represents the weight average molecular weight, as measured by gel permeation chromotagraphy, of the chitosan; and Mn represents the number average molecular weight, as measured by gel permeation chromotagraphy, of the chitosan. Chitosans A-F were obtained from the Vanson Company of the United States. Chitosan G was obtained from Ajinomoto Co. Inc. of Japan.

TABLE 1

|  | D.A. | Viscosity (cps) | Mw | Mn |
|---|---|---|---|---|
| Chitosan A | 0.07 | 170 | 880,000 | 330,000 |
| Chitosan B | 0.21 | 1,400 | 2,000,000 | 790,000 |
| Chitosan C | 0.15 | 3,500 | 3,500,000 | 1,700,000 |
| Chitosan D | 0.14 | 11,400 | — | — |
| Chitosan E | 0.17 | 3,600 | 2,650,000 | 900,000 |
| Chitosan F | 0.21 | 3,000 | 1,744,000 | 570,000 |
| Chitosan G | 0.20 | 1,100 | — | — |

Example 1

Samples of Chitosan B (4.5 grams) were mixed with about 188 grams of aqueous solutions of various acids. The mixtures were stirred for several hours during which the chitosan reacted with the acids to form chitosan salts which dissolved into the solution. The equilibrium pH of the mixture was measured after dissolution of the chitosan salt into the solution. The obtained liquid mixtures were then treated with various amounts of a 2.5 weight per cent aqueous solution of glutaraldehyde homogenized by thoroughly stirring by hand and then air dried at about 23° C. for about 16 hours on a Petri dish. After such drying, the solid materials were ground in a Waring blender and a fraction of particulates (300 micrometers to 600 micrometers) was collected for each sample for measurement of the AUL. The AUL measurements, type of acid used, the equilibrium pH of the mixture, and the amount of glutaraldehyde solution used, given as a weight percent based on the weight of chitosan used, for these samples are shown in Table 2.

TABLE 2

| Acid used | pH | Amount of glutaraldehyde (weight %) | Initial AUL (g/g) |
|---|---|---|---|
| Hydrochloric | 5.2 | 0.35 | 17.6 |
| Hydrochloric | 5.2 | 0.9 | 17.6 |
| Hydrochloric | 5.4 | 1.6 | 15.1 |
| Hydrochloric | 3.1 | 1.8 | 15.6 |
| Hydrochloric | 1.1 | 0.9 | 7.3 |
| Hydrochloric | 1.1 | 1.8 | 11.0 |
| Hydrochloric | 1.1 | 2.7 | 11.8 |
| Hydrochloric | 1.1 | 3.5 | 8.0 |
| Hydrochloric | 0.7 | 1.3 | 6.0 |
| Hydrochloric | 0.7 | 2.3 | 7.5 |
| Hydrochloric | 0.7 | 2.6 | 7.0 |
| Formic | 3.7 | 0.9 | 14.1 |
| Formic | 3.7 | 1.8 | 13.6 |
| Formic | 3.7 | 2.7 | 13.3 |
| Acetic | 4.9 | 0.9 | 17.3 |
| Acetic | 4.9 | 1.8 | 15.5 |
| Acetic | 4.9 | 2.7 | 15.4 |
| Acetic | 1.5 | 0.9 | 8.0 |
| Acetic | 1.5 | 2.7 | 9.5 |
| Acetic | 1.5 | 11.0 | 7.0 |
| Propionic | 5.5 | 1.8 | 14.6 |
| Citric | 2.4 | 1.8 | 3.8 |
| Citric | 4.0[a] | 1.8 | — |

[a]Chitosan was not completely soluble in the citric acid solution at pH 4

Example 2

Various chitosans (4.5 grams) were mixed with about 188 grams of aqueous solutions of hydrochloric acid. The mixtures were stirred for several hours during which the chitosan reacted with the acid to form chitosan hydrochloride which dissolved into the solution. The solutions all had an equilibrium pH between about 5.0 and 5.5. The obtained liquid mixtures were then treated with various amounts of a 2.5 weight percent aqueous solution of glutaraldehyde, homogenized by thoroughly stirring by hand, and then air dried at about 23° C. for about 16 hours on a Petri dish. After such drying, the solid materials were ground in a Waring blender and a fraction of particulates (300 micrometers to 600 micrometers) was collected for each sample for measurement of the AUL. The AUL measurements and the amount of glutaraldehyde solution used for these samples are shown in Table 3.

TABLE 3

| Starting Chitosan Material | Amount of glutaraldehyde (weight %) | Initial AUL (g/g) |
| --- | --- | --- |
| Chitosan A | 0.7 | 11.7 |
| Chitosan A | 1.1 | 9.9 |
| Chitosan A | 2.2 | 8.1 |
| Chitosan B | 0.35 | 17.6 |
| Chitosan B | 0.9 | 17.6 |
| Chitosan B | 1.6 | 15.1 |
| Chitosan C | 0.35 | 24.1 |
| Chitosan C | 0.7 | 20.3 |
| Chitosan C | 1.1 | 17.5 |

Example 3

Chitosan C (4.5 grams) was mixed with about 188 grams of aqueous solution of hydrochloric acid. The mixtures were stirred for several hours during which the chitosan reacted with the acid to form chitosan hydrochloride which dissolved into the solution. The solutions all had an equilibrium pH between about 5.0 and 5.5. The obtained liquid mixture was then treated with various amounts of aqueous solutions of various crosslinking agents. The mixture was then homogenized by thoroughly stirring by hand and then air dried at about 23° C. for about 16 hours on a Petri dish. After such drying, the solid materials were ground in a Waring blender and a fraction of particulates (300 micrometers to 600 micrometers) was collected for each sample for measurement of the AUL. The AUL measurements and the crosslinker type and amount for these samples, given as a weight percent based on the weight of chitosan used, are shown in Table 4. In Table 4, the number in parentheses after some of the names of the crosslinking agents refers to the average molecular weight of that particular crosslinking agent. The carboxymethyl cellulose had a degree of carboxymethyl substitution of about 0.8 and exhibited a Brookfield viscosity at about 25° C. as a 4 weight percent aqueous solution of about 35 centipoise.

TABLE 4

| Kind of Crosslinker | Amount of crosslinker (weight %) | AUL (g/g) |
| --- | --- | --- |
| Glutaraldehyde | 0.35 | 24.1 |
| Carboxymethyl Cellulose | 1.5 | 14.7 |
| Poly(ethylene glycol) diglycidal ether (200) | 0.3 | 15.0 |
| Poly(ethylene glycol) diglycidal ether (400) | 0.5 | 17.0 |
| Bis[polyoxyethylene bis(glycidyl ether)] (20,000) | 10 | 16.0 |
| $CuSO_4$ | 5 | 14.8 |

Example 4

Chitosan B (8.5 g) was heated at 85° C. for 1 hour and was then dispersed in a mixture (200 mL) of 80 volume per cent isopropanol and 20 volume percent water. An aqueous solution (2.5 g) of hydrochloric acid having a weight percent concentration of 37 was then dropped into the slurry under constant mechanical stirring until the mixture had an equilibrium pH of about 4.7. The slurry was subsequently left for 3 hours, filtered and dried. The obtained insoluble chitosan salt was then dispersed in water at a concentration of 2 weight percent to make a translucent dispersion which was then air dried at about 23° C. for about 16 hours. After such drying, the solid material was ground in a Waring blender and a fraction of particulates (300 micrometers to 600 micrometers) had an initial AUL of 15.0 g/g.

Example 5

Samples of various chitosans (20 grams) were individually added into 1000 ml of distilled water to form a 2% suspension. Acetic acid (8.5 grams) or formic acid (5.7 grams) was added into the suspension while stirring. The resulting mixtures containing water, chitosan, and acid were then thoroughly mixed for at least 5 hours at 23° C. The equilibrium pH of the mixture was then measured. The completely dissolved chitosan salt was recovered from the solution by evaporative drying at 50° C. in a Blue M air-convection oven. After drying, the recovered chitosan salt was ground into granules in a blender and heat treated at various temperatures for specific times. The initial Absorbency Under Load values of the various chitosan salts so prepared were measured. The exact combination of chitosan and acid and its peak AUL value are set forth in Table 5.

TABLE 5

| Starting Chitosan Material | Chitosan pH Salt | Heat Temp. (°C.) | Initial AUL (g/g) | | | | | | |
| --- | --- | --- | --- | --- | --- | --- | --- | --- | --- |
| | | | 0 min | 5 min | 10 min | 15 min | 20 min | 25 min | 30 min |
| Chitosan D | 5.6 Formate | 100 | 6.9 | 13.5 | 15.7 | 18.9 | 22.1 | 24.3 | 22.6 |
| | 5.5 Acetate | 90 | 7.8 | 14.5 | 18.6 | 20.4 | 22.5 | 21.5 | 20.4 |
| Chitosan C | 5.7 Formate | 100 | 6.6 | 10.3 | 13.5 | 16.2 | 21.8 | 22.4 | 20.4 |
| | 5.5 Acetate | 90 | 15.7 | 17.4 | 18.5 | 19.3 | 20.9 | 18.3 | 16.9 |
| Chitosan E | 5.0 Formate | 100 | 8.7 | 15.3 | 18.9 | 21.5 | 20.4 | 19.2 | — |
| | 5.0 Acetate | 90 | 13.2 | 16.4 | 18.7 | 19.1 | 17.5 | 14.3 | — |
| Chitosan F | 5.5 Formate | 90 | 12.4 | 18.0 | 20.4 | 20.7 | 22.3 | 21.6 | 20.2 |
| | 5.5 Acetate | 90 | 14.2 | 19.4 | 16.2 | 13.4 | 10.8 | — | — |
| Chitosan G | 5.0 Formate | 110 | 5.7 | 11.4 | 13.5 | 14.6 | 16.9 | 14.2 | 12.1 |
| | 4.8 Acetate | 90 | 10.2 | 12.0 | 14.3 | 15.2 | 11.3 | 9.8 | — |

Example 6

Samples of Chitosan C and Chitosan F (20 grams) were individually added into 1000 ml of distilled water to form a 2% suspension. Formic acid (5.7 grams), 7.2 grams of acetic acid, 8.7 grams of propionic acid, 11.7 grams of 37 wt % of hydrochloric acid, 11.6 grams of phosphoric acid, 15.6 grams of glutaric acid, or 22.7 grams of citric acid were separately added into respective suspensions with agitation. Molar ratio of the acid to chitosan is 1 to 1. The resulting mixtures containing water, chitosan, and acid were then thoroughly mixed for at least 8 hours at about 23° C. The equilibrium pH of the mixture was then measured. The completely dissolved chitosan salt was recovered from the solution by evaporative drying at 40° C. in a Blue M air-convection oven. After drying, the recovered chitosan salt was ground into granules in a blender and heat treated at various temperatures for specific times. The initial Absorbency Under Load values of the various chitosan salts so prepared were measured. The exact combination of chitosan and acid and its initial AUL value are set forth in Table 6.

(about 23° C.)) for two days before measuring the aged AUL. The initial and aged Absorbency Under Load values of the various chitosan salts so prepared are measured. The exact combination of chitosan and acid and its AUL value are set forth in Table 7.

TABLE 7

| Time of Aging (Days) | Chitosan Hydrochloride | AUL (g/g) Chitosan Formate | Chitosan Acetate | Chitosan Propionate |
|---|---|---|---|---|
| 0 | 8.1 | 12.4 | 14.2 | 13.8 |
| 5 | 8.5 | 15.8 | 7.3 (H) | 4.2 (H) |
| 10 | 10.9 | 16.3 | 6.3 (H) | |
| 20 | 13.7 | 14.3 | | |
| 30 | 15.8 | | 10.1 (H) | |
| 40 | 16.7 | | | |

(H) stands for very hard chitosan gel even after being fully saturated.

TABLE 6

| Chitosan Salt | pH | Temp. (°C.) | Initial AUL (g/g) | | | | | | | | | | | |
|---|---|---|---|---|---|---|---|---|---|---|---|---|---|---|
| | | | 0 min | 5 min | 10 min | 15 min | 20 min | 30 min | 40 min | 50 min | 60 min | 70 min | 80 min | 90 min |
| Formate | | | | | | | | | | | | | | |
| Chitosan C | 5.7 | 90 | 6.6 | — | 9.4 | — | 9.9 | 13.2 | 16.3 | 20.7 | 22.2 | 23.6 | 21.7 | 20.1 |
| Chitosan F | 5.5 | 90 | 12.4 | 18.0 | 20.4 | 20.7 | 22.3 | 20.2 | 18.2 | | | | | |
| Acetate | | | | | | | | | | | | | | |
| Chitosan C | 5.5 | 90 | 15.7 | 17.4 | 18.5 | 19.3 | 20.9 | 16.9 | | | | | | |
| Chitosan F | 5.5 | 90 | 13.2 | 19.4 | 16.2 | 13.4 | 10.8 | | | | | | | |
| Propionate | | | | | | | | | | | | | | |
| Chitosan C | 5.3 | 90 | 15.4 | 10.9 | 8.7 | 7.4 | 6.3 | | | | | | | |
| Chitosan F | 5.5 | 90 | 13.8 | 9.1 | 7.3 | 5.0 | | | | | | | | |
| Hydrochloride | | | | | | | | | | | | | | |
| Chitosan C Phosphate | 4.0 | 150 | 7.8 | 7.5 | 7.6 | 6.8 | 6.3 | 6.4 | | | | | | |
| Chitosan C Glutamate | 4.5 | 150 | 8.4 | 8.1 | 7.8 | 7.5 | 7.2 | 6.8 | | | | | | |
| Chitosan F Citrate | 5.0 | 120 | 8.0 | 7.8 | 6.1 | 5.3 | 4.1 | | | | | | | |
| Chitosan C | 4.8 | 100 | 8.7 | 8.2 | 7.0 | 6.2 | 5.3 | | | | | | | |

Example 7

Samples of Chitosan F (20 grams) were added into 1000 ml of distilled water to form a 2% suspension. Formic acid (5.7 grams), 7.1 grams of acetic acid, 8.7 grams of propionic acid, or 11.7 grams of 37 wt % hydrochloric acid was added into the suspension with agitation. The molar ratio of the acid to chitosan was about 1 to 1. The resulting mixtures containing water, chitosan, and acid were then thoroughly mixed for at least 8 hours at 23° C. The equilibrium pH of each mixture was then measured. The mixture containing hydrochloric acid had an equilibrium pH of about 4.3. The mixtures containing the other acids each had an equilibrium pH of about 5.5. The completely dissolved chitosan salt was recovered from the solution by evaporative drying at 40° C. in a Blue M air-convection oven. After drying, the recovered chitosan salt is ground into granules in a blender and placed in a chamber, which has a relative humidity of 100% at room temperature (about 23° C.), and aged for 5, 10, 20, 30 and 40 days. The aged chitosan salts were then dried at ambient condition (30% to 50% relative humidity, room temperature

Example 8

Samples of Chitosan C (20 grams) were added into 1000 ml of distilled water to form 2 weight percent suspensions. Formic acid (5.7 grams), acetic acid (7.1 grams), or a mixture of acids (4.3 g formic acid/2.9 g 37% HCL, 2.8 g formic acid/5.9 g 37% HCL, 5.3 g acetic acid/2.9 g 37% HCL, or 3.5 g acetic acid/5.9 g 37% HCL) were separately added into the suspensions with agitation. The molar ratio of acid or mixture of acids to amino group of chitosan was about 1 to 1. The resulting mixtures containing water, chitosan, and acid were then thoroughly mixed for at least 8 hours at 23° C. The equilibrium pH of the mixtures were then measured. All of the mixtures had an equilibrium pH between about 5.0 and about 5.5. The completely dissolved chitosan salt was recovered from the solution by evaporative drying at 40° C. in a Blue M air-convection oven. After drying, the recovered chitosan salts were ground into granules in a blender and heat treated at 90° C. for a sufficient time. The initial Absorbency Under Load values of the various chitosan salts so prepared are measured. The heat treated chitosan salts are placed in a chamber, which has a relative humidity of 100% at room temperature, and aged for 5, 10, 20 and 30 days. The aged chitosan salts are then dried at ambient conditions (about 30 percent to about 50 percent relative humidity at room temperature (about 23° C.)) for two days before measuring AUL. The exact combination of chitosan and acid and its initial or aged AUL value are set forth in Table 8.

TABLE 8

| Time of Aging (Days) | AUL (g/g) | | | | | |
|---|---|---|---|---|---|---|
| | Chitosan Formate | Chitosan HCOOH/HCL (3:1) | Chitosan HCOOH/HCL (1:1) | Chitosan Acetate | Chitosan HAc/HCL (3:1) | Chitosan HAc/HCL (1:1) |
| 0 | 22.2 | 20.5 | 19.8 | 20.9 | 19.2 | 17.1 |
| 10 | 18.8 | 18.1 | 18.6 | 14.3 | 16.7 | 14.9 |
| 20 | 14.3 | 17.2 | 17.8 | 6.8 | 14.6 | 14.1 |
| 30 | 10.1 | 14.1 | 16.2 | — | — | — |

Example 9

A sample of Chitosan D (20 grams) was suspended in 900 ml of distilled water with stirring. Thirty milliliters of mixed acid solution having a concentration of 1M acetic acid and 1M hydrochloric acid was added to the stirred chitosan suspension at room temperature (about 23° C.). After 10 hours of mixing, the chitosan salt solution was titrated with the above-mentioned mixed acid solution until a transparent solution of chitosan salt having an equilibrium pH range of between about 5.2 and about 5.5 was obtained. The concentration of the chitosan salt solution was about 2 weight percent. Then, 0.026 gm of citric acid as a crosslinking agent (dissolved in 10 ml of distilled water) was added to the chitosan salt solution. In some cases, 0.013 gm of sodium hypophosphite was also added as a crosslinking catalyst. The solution is mixed well at 23° C., poured into Teflon-lined trays, and dried in a convection oven at 40° C. for about 24 hours. Physical measurements of the chitosan salt generally indicate that substantially no crosslinking has occurred at this point. After grinding and sieving, the 300–600 micrometer size fraction is cured at various temperatures for various lengths of time. The AUL results are set forth in Table 9.

The chitosan salt sample that was prepared without the sodium hypophosphite catalyst was cured at 100° C. for 60 minutes and was evaluated for AUL age-stability. The chitosan salt was treated for 10 days in a 100 percent relative humidity environment at about 23° C. The aged chitosan salt exhibited an AUL of 16.1 g/g.

TABLE 9

| Curing Temp. (°C.) | Citric Acid: Sodium Hypophosphite weight ratio | Initial AUL (g/g) After Curing for Various Time Periods (min) | | | | | |
|---|---|---|---|---|---|---|---|
| | | 10 | 20 | 30 | 40 | 60 | 80 |
| 50 | 1:0 | — | — | — | 8.6 | — | — |
| 90 | 1:0 | — | — | — | 12.5 | — | — |
| 100 | 1:0 | — | 17 | 18 | 18.8 | 20.1 | 19.3 |
| 100 | 1:0.5 | 16 | 18.1 | 18.5 | 20.5 | 19.5 | — |
| 110 | 1:0 | 17.8 | 18 | 18.5 | 19 | 17 | 15.1 |
| 110 | 1:0.5 | 18 | 19.1 | 19.5 | 19.7 | 16.5 | — |
| 130 | 1:0 | 14.2 | 12.4 | 12.5 | 12.2 | 11.5 | 11.3 |
| 150 | 1:0 | — | — | — | 10.8 | — | — |

While the present invention has been described in terms of the specific embodiments described above, numerous equivalent changes and modifications will be clear to those skilled in the art. Accordingly, the specific examples set forth above are not intended to limit in any manner the scope of the invention as set forth in the appended claims.

What is claimed is:

1. A process for preparing a water-swellable, water-insoluble chitosan salt, the process comprising:

forming a mixture comprising a water-insoluble chitosan, water, and an add selected from the group consisting of monobasic acids having a $pKa_1$ less than about 6 and multibasic acids having a $pKa_1$ less than about 6 and all $pKa_n$ greater than about 5.5, wherein n is an integer greater than 1, wherein the mixture has an equilibrium pH between about 2 and about 6.5, and wherein the mixture is prepared under conditions effective to form a water-soluble chitosan salt, wherein the water-soluble chitosan salt dissolves into the water to form a homogeneous mixture; and recovering the chitosan salt from the homogeneous mixture, wherein the recovered chitosan salt is water swellable and water insoluble and exhibits an initial Absorbency Under Load value of at least about 14 grams per gram.

2. The process according to claim 1 wherein the chitosan has an average degree of acetylation of from 0 to about 0.5.

3. The process according to claim 1 wherein the chitosan salt is chitosan hydrochloride, chitosan hydrobromide, chitosan phosphate, chitosan formate, chitosan acetate, chitosan propionate, chitosan chloroacetate, chitosan hydroxyacetate, chitosan butyrate, chitosan isobutyrate, chitosan acrylate, or mixtures thereof.

4. The process according to claim 1 wherein the chitosan salt is chitosan hydrochloride, chitosan formate, chitosan acetate, chitosan propionate, or mixtures thereof.

5. The process according to claim 1 wherein the acid is acetic acid, acrylic acid, n-butyric acid, iso-butyric acid, chloroacetic acid, formic acid, hydrobromic acid, hydrochloric acid, hydroxy acetic acid, propionic acid, phosphoric acid, or mixtures thereof.

6. The process according to claim 5 wherein the acid is hydrochloric acid, formic acid, acetic acid, propionic acid, or mixtures thereof.

7. The process according to claim 1 wherein the mixture further comprises a crosslinking agent and the crosslinking agent is recovered with the chitosan salt.

8. The process according to claim 7 wherein the crosslinking agent is selected from the group consisting of (a) compound comprising at least two functional groups capable of reacting with an amido, amino, or hydroxyl group of a chitosan salt and (b) a metal ion with at least two positive charges and which is effective to form coordination bonds with the chitosan salt.

9. The process according to claim 7 wherein said crosslinking agent is selected from the group consisting of dialdehydes, multicarboxylic acids, diepoxides, and mixtures thereof.

10. The process according to claim 7 wherein the crosslinking agent is selected from the group consisting of glutaraldehyde, citric acid, butane tetracarboxylic acid, carboxymethyl cellulose, poly(ethylene glycol) diglycidal ether, and bis[polyoxyethylene bis(glycidyl ether)], and mixtures thereof.

11. The process according to claim 7 wherein said crosslinking agent is a multibasic acid having both a $pKa_1$ and a $pKa_2$ that are both less than about 5.5.

12. The process according to claim 11 wherein said crosslinking agent is adipic acid, butane tetracarboxylic acid, citric acid, glutaric acid, itaconic acid, malic acid, succinic acid, or mixtures thereof.

13. The process according to claim 7 wherein said crosslinking agent comprises a metal ion selected from the group consisting of $Cu^{2+}$, $Fe^{3+}$, $Ce^{3+}$, $Ti^{4+}$, and $Ce^{4+}$.

14. The process according to claim 13 wherein said crosslinking agent is selected from the group consisting of $CuSO_4$, $FeCl_3$, $Ce_2(SO_4)_3$, $ZrCl_4$, $Ce(NH_4)_4(SO_4)_4.2H_2O$, and mixtures thereof.

15. The process of claim 1 further comprising treating said recovered chitosan salt at a temperature above about 50° C. for a time effective to render said chitosan salt water swellable and water insoluble.

16. The process according to claim 15 wherein said chitosan salt is treated at a temperature of from about 50° C. to about 250° C. for a time of from about 1 minute to about 600 minutes.

17. The process according to claim 1 wherein the chitosan and water are first mixed together and then the acid is added to the mixture.

18. The process according to claim 1 wherein the process further comprises treating the chitosan salt under humid conditions for a time effective to render said chitosan salt water swellable and water insoluble.

19. The process according to claim 18 wherein said chitosan salt is treated at a humidity of from about 75 percent relative humidity to about 100 percent relative humidity for a time of from about 1 day to about 60 days.

20. The process according to claim 1 wherein said chitosan salt is recovered by evaporative drying.

21. The process according to claim 20 wherein said evaporative drying is done at a temperature from about 10° C. to about 100° C.

22. The process according to claim 1 wherein said chitosan salt is recovered by precipitation.

23. The process according to claim 1 wherein said mixture has an equilibrium pH between about 2.5 to about 6.

24. The process according to claim 23 wherein said mixture has an equilibrium pH between about 4 to about 6.

25. The process according to claim 1 wherein the water-swellable, water-insoluble chitosan salt exhibits an initial Absorbency Under Load value of at least about 17 grams per gram.

26. The process according to claim 25 wherein the water-swellable, water-insoluble chitosan salt exhibits an initial Absorbency Under Load value of at least about 20 grams per gram.

27. The process according to claim 1 wherein the water-swellable, water-insoluble chitosan salt retains at least about 50 percent of the initial Absorbency Under Load value after aging for about 60 days at about 24° C. and at least about 30 percent relative humidity.

28. The process according to claim 1 wherein the water-swellable, water-insoluble chitosan salt retains at least about 50 percent of the initial Absorbency Under Load value after aging for about 20 days at about 24° C. and at about 100 percent relative humidity.

29. A process for preparing a water-swellable, water-insoluble chitosan salt, the process comprising:

forming a mixture comprising a water-insoluble chitosan wherein the chitosan has an average degree of acetylation of from 0 to about 0.5, water, and an acid selected from the group consisting of hydrochloric acid, formic acid, acetic acid, propionic acid, and mixtures thereof, wherein the mixture has an equilibrium pH between about 2 and about 6.5, and wherein the mixture is prepared under conditions effective to form a water-soluble chitosan salt, wherein the water-soluble chitosan salt dissolves into the water to form a homogeneous mixture; and recovering the chitosan salt from the homogeneous mixture, wherein the recovered chitosan salt is water swellable and water insoluble and exhibits an initial Absorbency Under Load value of at least about 14 grams per gram.

30. A process for preparing a water-swellable, water-insoluble chitosan salt, the process comprising:

forming a mixture comprising a water-insoluble chitosan, water, and an acid selected from the group consisting of monobasic acids having a $pKa_1$ less than about 6 and multibasic acids having a $pKa_1$ less than about 6 and all $pKa_n$ greater than about 5.5, wherein n is an integer greater than 1, wherein the mixture has an equilibrium pH between about 2 and about 6.5, and wherein the mixture is prepared under conditions effective to form a water-soluble chitosan salt, wherein the water-soluble chitosan salt dissolves into the water to form a homogeneous mixture; and recovering said water-soluble chitosan salt from said homogeneous mixture; and treating said recovered chitosan salt at a temperature and for an amount of time effective to render said chitosan salt water swellable and water insoluble, wherein the water-swellable, water-insoluble chitosan salt exhibits an initial Absorbency Under Load value of at least about 14 grams per gram.

31. The process according to claim 30 wherein the chitosan has an average degree of acetylation of from 0 to about 0.5.

32. The process according to claim 30 wherein the chitosan salt is chitosan hydrochloride, chitosan hydrobromide, chitosan formate, chitosan phosphate, chitosan acetate, chitosan propionate, chitosan chloroacetate, chitosan hydroxyacetate, chitosan butyrate, chitosan isobutyrate, chitosan acrylate, or mixtures thereof.

33. The process according to claim 30 wherein the acid is acetic acid, acrylic acid, n-butyric acid, iso-butyric acid, chloroacetic acid, formic acid, hydrobromic acid, hydrochloric acid, hydroxy acetic acid, propionic acid, phosphoric acid, or mixtures thereof.

34. The process according to claim 30 wherein the mixture further comprises a crosslinking agent and the crosslinking agent is recovered with the chitosan salt.

35. The process according to claim 34 wherein said crosslinking agent is selected from the group consisting of dialdehydes, multicarboxylic acids, diepoxides, and mixtures thereof.

36. The process according to claim 34 wherein the crosslinking agent is selected from the group consisting of glutaraldehyde, citric acid, butane tetracarboxylic acid, carboxymethyl cellulose, poly(ethylene glycol) diglycidal ether, and bis[polyoxyethylene bis(glycidyl ether)], and mixtures thereof.

37. The process according to claim 34 wherein said crosslinking agent is a multibasic acid having both a $pKa_1$ and a $pKa_2$ that are both less than about 5.5.

38. The process according to claim 37 wherein said crosslinking agent is adipic acid, butane tetracarboxylic acid, citric acid, glutaric acid, itaconic acid, malic acid, succinic acid, or mixtures thereof.

39. The process according to claim 34 wherein said crosslinking agent comprises a metal ion selected from the group consisting of $Cu^{2+}$, $Fe^{3+}$, $Ce^{3+}$, $Ti^{4+}$, $Zr^{4+}$, and $Ce^{4+}$.

40. The process according to claim 30 wherein said chitosan salt is treated at a temperature of from about 50° C. to about 250° C. for a time of from about 1 minute to about 600 minutes.

41. The process according to claim 30 wherein said mixture has an equilibrium pH between about 2.5 to about 6.

42. The process according to claim 41 wherein said mixture has an equilibrium pH between about 4 to about 6.

43. The process according to claim 30 wherein the water-swellable, water-insoluble chitosan salt exhibits an initial Absorbency Under Load value of at least about 17 grams per gram.

44. The process according to claim 43 wherein the water-swellable, water-insoluble chitosan salt exhibits an initial Absorbency Under Load value of at least about 20 grams per gram.

45. The process according to claim 30 wherein the water-swellable, water-insoluble chitosan salt retains at least about 50 percent of the initial Absorbency Under Load value after aging for about 60 days at about 24° C. and at least about 30 percent relative humidity.

46. The process according to claim 30 wherein the water-swellable, water-insoluble chitosan salt retains at least about 50 percent of the initial Absorbency Under Load value after aging for about 20 days at about 24° C. and at about 100 percent relative humidity.

47. A process for preparing a water-swellable, water-insoluble chitosan salt, the process comprising:

forming a mixture comprising a water-insoluble chitosan, water, and an acid selected from the group consisting of monobasic acids having a $pKa_1$ less than about 6 and multibasic acids having a $pKa_1$ less than about 6 and all $pKa_n$ greater than about 5.5, wherein n is an integer greater than 1, wherein the mixture has an equilibrium pH between about 2 and about 6.5, and wherein the mixture is prepared under conditions effective to form a water-soluble chitosan salt, wherein the water-soluble chitosan salt dissolves into the water to form a homogeneous mixture; and recovering said water-soluble chitosan salt from said homogeneous mixture; and treating said recovered chitosan salt at a humid condition and for an amount of time effective to render said chitosan salt water swellable and water insoluble, wherein the water-swellable, water-insoluble chitosan salt exhibits an initial Absorbency Under Load value of at least about 14 grams per gram.

48. The process according to claim 47 wherein the chitosan has an average degree of acetylation of from 0 to about 0.5.

49. The process according to claim 47 wherein the chitosan salt is chitosan hydrochloride, chitosan hydrobromide, chitosan phosphate, chitosan formate, chitosan acetate, chitosan propionate, chitosan chloroacetate, chitosan hydroxy-acetate, chitosan butyrate, chitosan isobutyrate, chitosan acrylate, or mixtures thereof.

50. The process according to claim 47 wherein the acid is acetic acid, acrylic acid, n-butyric acid, iso-butyric acid, chloroacetic acid, formic acid, hydrobromic acid, hydrochloric acid, hydroxy acetic acid, propionic acid, phosphoric acid, or mixtures thereof.

51. The process according to claim 47 wherein the mixture further comprises a crosslinking agent and the crosslinking agent is recovered with the chitosan salt.

52. The process according to claim 51 wherein said crosslinking agent is selected from the group consisting of dialdehydes, multicarboxylic acids, diepoxides, and mixtures thereof.

53. The process according to claim 51 wherein the crosslinking agent is selected from the group consisting of glutaraldehyde, citric acid, butane tetracarboxylic acid, carboxymethyl cellulose, poly(ethylene glycol) diglycidal ether, and bis[polyoxyethylene bis(glycidyl ether)], and mixtures thereof.

54. The process according to claim 51 wherein said crosslinking agent is a multibasic acid having both a $pKa_1$ and a $pKa_2$ that are both less than about 5.5.

55. The process according to claim 54 wherein said crosslinking agent is adipic acid, butane tetracarboxylic acid, citric acid, glutaric acid, itaconic acid, malic acid, succinic acid, or mixtures thereof.

56. The process according to claim 51 wherein said crosslinking agent comprises a metal ion selected from the group consisting of $Cu^{2+}$, $Fe^{3+}$, $Ce^{3+}$, $Ti^{4+}$, $Zr^{4+}$, and $Ce^{4+}$.

57. The process according to claim 47 wherein said chitosan salt is treated at a humidity of from about 75 percent relative humidity to about 100 percent relative humidity for a time of from about 1 day to about 60 days.

58. The process according to claim 47 wherein said mixture has an equilibrium pH between about 2.5 to about 6.

59. The process according to claim 58 wherein said mixture has an equilibrium pH between about 4 to about 6.

60. The process according to claim 47 wherein the water-swellable, water-insoluble chitosan salt exhibits an initial Absorbency Under Load value of at least about 17 grams per gram.

61. The process according to claim 60 wherein the water-swellable, water-insoluble chitosan salt exhibits an initial Absorbency Under Load value of at least about 20 grams per gram.

62. The process according to claim 47 wherein the water-swellable, water-insoluble chitosan salt retains at least about 50 percent of the initial Absorbency Under Load value after aging for about 60 days at about 24° C. and at least about 30 percent relative humidity.

63. The process according to claim 47 wherein the water-swellable, water-insoluble chitosan salt retains at least about 50 percent of the initial Absorbency Under Load value after aging for about 20 days at about 24° C. and at about 100 percent relative humidity.

64. A process for preparing a water-swellable, water-insoluble chitosan salt comprising:

a. preparing a mixture comprising a chitosan comprising an original crystalline structure, water, an acid selected from the group consisting of monobasic acids having a pKa less than about 6 and multibasic acids having a $pKa_1$ less than about 6 and all $pKa_n$ greater than about 5.5, wherein n is an integer greater than 1, and a nonsolvent that is miscible with water and in which both chitosan and the chitosan salt to be formed are insoluble, wherein the water and the nonsolvent are used in amounts in the mixture effective to result in the chitosan and the chitosan salt to be formed not being soluble in the mixture, wherein the mixture has an equilibrium pH between about 2 and about 6.5, and wherein the mixture is prepared under conditions effective to form a chitosan salt, wherein the chitosan salt comprises an amount of the original crystalline structure of the chitosan and a non-crystalline structure;

b. recovering the chitosan salt from the mixture; and c. preparing a second mixture comprising the recovered chitosan salt and water, wherein the chitosan salt is dispersed in the water and the non-crystalline structure of the chitosan salt dissolves into the water, and d. recovering the chitosan salt from the second mixture, wherein the chitosan salt comprises an amount of the original crystalline structure of the chitosan to be effective to result in the chitosan salt being water swellable and water insoluble and exhibiting an initial Absorbency Under Load value of at least about 14 grams per gram.

65. The process according to claim 64 wherein the chitosan salt has an average degree of acetylation of from 0 to about 0.5.

66. The process according to claim 64 wherein the chitosan salt is chitosan hydrochloride, chitosan hydrobromide, chitosan phosphate, chitosan formate, chitosan acetate, chitosan propionate, chitosan chloroacetate, chitosan hydroxyacetate, chitosan butyrate, chitosan isobutyrate, chitosan acrylate, or mixtures thereof.

67. The process according to claim 64 wherein the acid is acetic acid, acrylic acid, n-butyric acid, iso-butyric acid, chloroacetic acid, formic acid, hydrobromic acid, hydrochloric acid, hydroxy acetic acid, propionic acid, phosphoric acid, or mixtures thereof.

68. The process according to claim 64 wherein the nonsolvent is methanol, ethanol, acetone, isopropanol, dioxane, glycerol, ethylene glycol, propylene glycol, butanol, pentanol, hexanol, or mixtures thereof.

69. The process according to claim 64 wherein the chitosan salt is recovered from the mixture by evaporative drying.

70. The process according to claim 64 wherein the water-swellable, water-insoluble chitosan salt exhibits an initial Absorbency Under Load value of at least about 17 grams per gram.

71. The process according to claim 70 wherein the water-swellable, water-insoluble chitosan salt exhibits an initial Absorbency Under Load value of at least about 20 grams per gram.

72. The process according to claim 64 wherein the water-swellable, water-insoluble chitosan salt retains at least about 50 percent of the initial Absorbency Under Load value after aging for about 60 days at about 24° C. and at least about 30 percent relative humidity.

73. The process according to claim 64 wherein the water-swellable, water-insoluble chitosan salt retains at least about 50 percent of the initial Absorbency Under Load value after aging for about 20 days at about 24° C. and at about 100 percent relative humidity.

74. The process according to claim 64 wherein the mixture further comprises a crosslinking agent and the crosslinking agent is recovered with the chitosan salt.

75. A water-swellable, water-insoluble chitosan salt wherein the chitosan salt exhibits an initial Absorbency Under Load value of at least about 14 grams per gram.

76. The chitosan salt of claim 75 wherein the chitosan salt is chitosan hydrochloride, chitosan hydrobromide, chitosan phosphate, chitosan formate, chitosan acetate, chitosan propionate, chitosan chloroacetate, chitosan hydroxyacetate, chitosan butyrate, chitosan isobutyrate, chitosan acrylate, or mixtures thereof.

77. The chitosan salt of claim 76 wherein the chitosan salt is chitosan hydrochloride, chitosan formate, chitosan acetate, chitosan propionate or mixtures thereof.

78. The chitosan salt of claim 75 wherein the chitosan salt has average degree of acetylation of from 0 to about 0.5.

79. The chitosan salt of claim 75 wherein the chitosan salt exhibits an initial Absorbency Under Load value of at least about 17 grams per gram.

80. The chitosan salt of claim 79 wherein the chitosan salt exhibits an initial Absorbency Under Load value of at least about 20 grams per gram.

81. The chitosan salt of claim 80 wherein the chitosan salt exhibits an initial Absorbency Under Load of at least about 24 grams per gram.

82. The chitosan salt of claim 81 wherein the chitosan salt exhibits an initial Absorbency Under Load of at least about 27 grams per gram.

83. The chitosan salt of claim 75 wherein the chitosan salt retains at least about 50 percent of the initial Absorbency Under Load value after aging for about 60 days at about 24° C. and at least about 30 percent relative humidity.

84. The chitosan salt of claim 83 wherein the chitosan salt retains at least about 70 percent of the initial Absorbency Under Load value after aging for about 60 days at about 24° C. and at least about 30 percent relative humidity.

85. The chitosan salt of claim 75 wherein the chitosan salt retains at least about 50 percent of the initial Absorbency Under Load value after aging for about 20 days at about 24° C. and at about 100 percent relative humidity.

86. The chitosan salt of claim 85 wherein the chitosan salt retains at least about 70 percent of the initial Absorbency Under Load value after aging for about 20 days at about 24° C. and at about 100 percent relative humidity.

87. A water-swellable, water-insoluble chitosan salt wherein the chitosan salt exhibits an initial Absorbency Under Load value of at least about 17 grams per gram and retains at least about 70 percent of the initial Absorbency Under Load value after aging for about 20 days at about 24° C. and at about 100 percent relative humidity, wherein the chitosan salt has an average degree of acetylation of from 0 to about 0.5, and wherein the chitosan salt has a viscosity in a 1.0 weight percent aqueous solution at 25° C. of from about 100 centipoise to about 80,000 centipoise.

88. A water-swellable, water-insoluble chitosan salt formed by the process of claim 1.

89. A water-swellable, water-insoluble chitosan salt formed by the process of claim 30.

90. A water-swellable, water-insoluble chitosan salt formed by the process of claim 47.

91. A water-swellable, water-insoluble chitosan salt formed by the process of claim 64.

92. A process for preparing a water-swellable, water-insoluble chitosan-salt, the process comprising:

forming a homogeneous mixture comprising a water-soluble chitosan salt and water; wherein the chitosan salt dissolves into the water; and recovering the chitosan salt from the homogeneous mixture, wherein the recovered chitosan salt is water swellable and water insoluble and exhibits an initial Absorbency Under Load value of at least about 14 grams per gram.

93. The process according to claim 92 wherein the chitosan salt is chitosan hydrochloride, chitosan hydrobromide, chitosan phosphate, chitosan formate, chitosan acetate, chitosan propionate, chitosan chloroacetate, chitosan hydroxyacetate, chitosan butyrate, chitosan isobutyrate, chitosan acrylate, or mixtures thereof.

94. The process according to claim 93 wherein the chitosan salt is chitosan hydrochloride, chitosan formate, chitosan acetate, chitosan propionate, or mixtures thereof.

95. The process of claim 92 further comprising treating said recovered chitosan salt at a temperature above about 50° C. for a time effective to render said chitosan salt water swellable and water insoluble.

96. The process according to claim 95 wherein said chitosan salt is treated at a temperature of from about 50° C. to about 250° C. for a time of from about 1 minute to about 600 minutes.

97. The process according to claim 92 wherein the process further comprises treating the chitosan salt under humid conditions for a time effective to render said chitosan salt water swellable and water insoluble.

98. The process according to claim 97 wherein said chitosan salt is treated at a humidity of from about 75 percent relative humidity to about 100 percent relative humidity for a time of from about 1 day to about 60 days.

99. The process according to claim 92 wherein said chitosan salt is recovered by evaporative drying.

100. The process according to claim 99 wherein said evaporative drying is done at a temperature from about 100° C. to about 100° C.

101. The process according to claim 92 wherein said chitosan salt is recovered by precipitation.

102. The process according to claim 92 wherein the water-swellable, water-insoluble chitosan salt exhibits an initial Absorbency Under Load value of at least about 17 grams per gram.

103. The process according to claim 102 wherein the water-swellable, water-insoluble chitosan salt exhibits an initial Absorbency Under Load value of at least about 20 grams per gram.

104. The process according to claim 92 wherein the water-swellable, water-insoluble chitosan salt retains at least about 50 percent of the initial Absorbency Under Load value after aging for about 60 days at about 24° C. and at least about 30 percent relative humidity.

105. The process according to claim 104 wherein the water-swellable, water-insoluble chitosan salt retains at least about 50 percent of the initial Absorbency Under Load value after aging for about 20 days at about 24° C. and at about 100 percent relative humidity.

* * * * *